(12) United States Patent
Woods

(10) Patent No.: US 7,963,967 B1
(45) Date of Patent: Jun. 21, 2011

(54) BONE PREPARATION TOOL

(75) Inventor: Michael Woods, Missoula, MT (US)

(73) Assignee: Woodse Enterprises, Inc., Missoula, MT (US)

( * ) Notice: Subject to any disclaimer, the term of this patent is extended or adjusted under 35 U.S.C. 154(b) by 494 days.

(21) Appl. No.: 11/871,818

(22) Filed: Oct. 12, 2007

Related U.S. Application Data

(60) Provisional application No. 60/829,232, filed on Oct. 12, 2006.

(51) Int. Cl.
A61B 17/00 (2006.01)
A61F 2/46 (2006.01)

(52) U.S. Cl. .............. 606/79; 606/84; 606/85; 606/86 R

(58) Field of Classification Search .............. 606/79–85, 606/86 R; 433/119, 165
See application file for complete search history.

(56) References Cited

U.S. PATENT DOCUMENTS

| | | | | |
|---|---|---|---|---|
| 5,257,632 A * | 11/1993 | Turkel et al. | .................. | 600/567 |
| 5,331,972 A * | 7/1994 | Wadhwani et al. | ........... | 600/567 |
| 5,665,093 A * | 9/1997 | Atkins et al. | .................. | 606/108 |
| 5,807,275 A * | 9/1998 | Jamshidi | ....................... | 600/567 |
| 5,928,239 A * | 7/1999 | Mirza | ............................. | 606/79 |
| 6,004,326 A | 12/1999 | Castro | | |
| 6,083,225 A | 7/2000 | Winslow | | |
| 6,241,734 B1 * | 6/2001 | Scribner et al. | ................. | 606/93 |
| 6,309,400 B2 * | 10/2001 | Beaupre | ........................ | 606/169 |
| 6,451,022 B2 | 9/2002 | Dinger | | |
| 6,582,439 B1 * | 6/2003 | Sproul | ............................ | 606/92 |
| 6,679,886 B2 * | 1/2004 | Weikel et al. | ................... | 606/79 |
| 6,740,090 B1 * | 5/2004 | Cragg et al. | .................... | 606/79 |
| 6,780,191 B2 * | 8/2004 | Sproul | ............................ | 606/92 |
| 6,875,219 B2 * | 4/2005 | Arramon et al. | ................ | 606/92 |
| 7,081,122 B1 * | 7/2006 | Reiley et al. | ................... | 606/185 |
| 7,241,297 B2 * | 7/2007 | Shaolian et al. | ................ | 606/80 |
| 7,318,826 B2 * | 1/2008 | Teitelbaum et al. | ............ | 606/80 |
| 7,399,306 B2 * | 7/2008 | Reiley et al. | ................... | 606/185 |
| 7,465,304 B1 * | 12/2008 | Haufe et al. | ..................... | 606/79 |
| 2002/0013594 A1 | 1/2002 | Dinger | | |
| 2002/0026195 A1 * | 2/2002 | Layne et al. | ...................... | 606/72 |
| 2002/0183758 A1 * | 12/2002 | Middleton et al. | .............. | 606/79 |
| 2002/0193758 A1 * | 12/2002 | Sandberg | ....................... | 604/304 |
| 2003/0050644 A1 | 3/2003 | Boucher | | |
| 2003/0199871 A1 | 10/2003 | Foley | | |
| 2004/0068264 A1 * | 4/2004 | Treace | ............................ | 606/86 |
| 2004/0087956 A1 | 5/2004 | Weikel | | |
| 2004/0087970 A1 * | 5/2004 | Chu et al. | ....................... | 606/119 |
| 2004/0092933 A1 * | 5/2004 | Shaolian et al. | ................ | 606/61 |
| 2004/0133208 A1 | 7/2004 | Weikel | | |
| 2004/0162559 A1 * | 8/2004 | Arramon et al. | ................ | 606/62 |
| 2004/0267164 A1 | 12/2004 | Rhodes | | |

(Continued)

Primary Examiner — Thomas C Barrett
Assistant Examiner — Matthew Lawson
(74) Attorney, Agent, or Firm — Sarah J. Rhoades

(57) ABSTRACT

A bone preparing tool for use with a percutaneous bone access system. The bone access system penetrates the interior of a bone. The bone preparation tool allows a surgeon to prepare the interior of a bone for therapeutic treatments. The tool includes a handle, flexible rod and, bone preparation tip, which may include an off-set wedge, a banana wedge, a tapered tip, and a pedestal tip. Each tip has specialized functionality in bone preparation. The flexible rod and specialized tip are inserted through a curved cannula and employed for bone preparation. This tool is useful when implementing a variety of bone therapeutic treatments which benefit from internal bone access and preparation. Current tools are limited and cannot properly be used on bone that is healed or hardened. This invention allows a transpedicular or extrapedicular approach to a bone and provides sufficient tensile strength but flexibility to affect optimum functionality.

6 Claims, 14 Drawing Sheets

U.S. PATENT DOCUMENTS

| | | |
|---|---|---|
| 2005/0043737 A1 | 2/2005 | Reiley |
| 2005/0119662 A1 | 6/2005 | Reiley |
| 2005/0209595 A1 | 9/2005 | Karmon |
| 2005/0234493 A1 | 10/2005 | Carr |
| 2005/0234496 A1 * | 10/2005 | Wells et al. ............ 606/185 |
| 2005/0240193 A1 | 10/2005 | Layne |
| 2005/0251145 A1 | 11/2005 | Desarzens |
| 2006/0064101 A1 * | 3/2006 | Arramon ............ 606/82 |

* cited by examiner

BONE PREPARATION TOOL

CROSS-REFERENCE TO RELATED APPLICATIONS

This patent application claims priority under 35 U.S.C. §119(e) to U.S. Patent Application Ser. No. 60/829,232, entitled "Bone Manipulating Tool" and filed on Oct. 12, 2006, which application is now pending. The entire disclosure of that provisional patent application is hereby incorporated by reference.

FIELD OF THE INVENTION

This invention relates to the treatment of bone conditions of the human and other animal body systems and, more particularly, to systems and methods for correcting bone conditions by accessing the interior structure of the bone via a percutaneous approach.

BACKGROUND OF THE INVENTION

The mineralized tissue of the bones of the human skeletal system are generally categorized into two morphological groups: "cortical" bone and "cancellous" bone. The outer walls of all bones are composed of cortical or "compact" bone. Cortical bone is characterized by a dense structure with only microscopic porosity. In contrast to cancellous bone, cortical bone tissue is much harder and denser. Cortical bone provides a protective layer and support for bones such as vertebral bodies. Cancellous or "trabecular" bone is found in the interior of bones. This tissue is composed of an interconnected framework and reinforcement called "trabeculae." Physicians have developed methodologies to treat bones by accessing their interior structure using a percutaneous approach. For example, they have artificially replenished the space left where trabeculae are lost due to collapse and/or compression of vertebral bodies.

These types of treatments are critical when a vertebral body collapses, commonly know as a compression fracture. Such injuries are often noted in individuals with osteoporosis or osteopenia as well as other diseases such as myeloma, a form of bone cancer. Osteoporosis is a disease of the bone that is most commonly found in the middle-aged and the elderly, particularly women. It is characterized by a gradual loss or demineralization of spongy cancellous bone, causing the remaining bone to become brittle and lose elasticity, thus rendering the bone weaker and more prone to fracture. Where osteoporosis has significantly weakened the cancellous bone, the cortical bone may be similarly affected and/or unable to solely support the loads placed on the spine, and thus the vertebral bodies become especially prone to fracture.

Vertebroplasty and Kyphoplasty are two minimally-invasive procedures that have been developed to access and treat diseased or fractured bone, such as collapsed or fractured vertebral bodies in individuals suffering from osteoporosis. These procedures require a bilateral approach into vertebral structures. In a vertebroplasty procedure, after the interior bone is accessed, poly-methylmethacrylate (PMMA) or bone cement is injected directly into the interior of a weakened and/or fractured bone in an attempt to reinforce the bone and prevent further weakening or fracture. In a Kyphoplasty procedure, a surgeon similarly accesses the interior of the bone with a bilateral approach. The surgeon then uses additional techniques and surgical tools to compact the cancellous bone and expand the cortical bone of the weakened and/or fractured vertebral body. Then the surgeon introduces a filler material such as bone cement into the bone. This procedure may prevent further fracture or subsidence of the bone.

Both of these procedures seek to alleviate the pain and discomfort experienced by patients suffering from vertebral compression fractures, and both procedures seek to reinforce a fractured and/or weakened vertebral body against further fracture. Both procedures include protocols for introducing filler material to form an "internal cast" to support the vertebral body against further overload.

Both of these techniques are invasive, but are considered minimally-invasive. The procedures employ an access tool or similar portal system such as a straight, rigid cannula having an interior lumen through which the interior of the bone is accessed. These access tools, which are typically designed to penetrate rigid tissue such as cortical bone, generally require significant column strength to penetrate and transit the rigid tissue and are thus essentially non-expandable. Consequently, the size of the inner lumen of such access tools basically defines the maximum dimensions of any therapeutic substance and/or surgical tool that can pass through the access tool into the vertebral body.

Because a vertebroplasty procedure does not currently call for the insertion of tools through the cannula and only calls for the injection of a flowable material such as bone cement into the fractured vertebral body, the lumen of the access tool necessary for introduction of such substances can be rather small. A common access tool used in a vertebroplasty procedure is an 11-gage spinal needle having an outer diameter of 0.120 inches and an interior lumen approximately 0.095 inches in diameter. Because the access tool for a vertebroplasty is of such small diameter, very little soft tissue and/or bone trauma is caused. The smaller access path allows the tool to be inserted through the pedicles in the vertebral bodies of the thoracic and lumbar regions of the human spine. The disadvantage of vertebroplasty is that surgeons are not able to affect change in the cancellous bone. Furthermore, the simple injection of filler necessitates use of higher pressures which can cause damage or an uncontrollable leakage of cement to a non-targeted, vital structure such as a nerve or blood vessel.

In contrast, a Kyphoplasty procedure employs tools, such as inflatable bone tamps, to compact the cancellous bone and move the cortical bone in an attempt to restore the vertebral body. These tools generally require a larger access path than that required for a typical vertebroplasty procedure. An access tool suitable for use in a Kyphoplasty procedure is approximately four times larger than a cannula used for vertebroplasty. Such larger tools, however, can potentially cause additional soft tissue and bone damage and may be unsuitable for insertion through smaller access paths, such as through the pedicles in the vertebral bodies of the thoracic and lumbar regions of the human spine.

A Kyphoplasty procedure has advantages over a vertebroplasty procedure; however, the tools that currently exist for creating a void within the bone have not been fully adapted to meet the needs of patients. The existing Kyphoplasty void-creation devices rely on a great degree of chance for preparing the bone. A surgeon does not have the control desired to designate the size and shape of the void created. Furthermore, the current tools do not provide sufficient strength to exert the needed force to affect vertebral bodies, particularly where a patient has suffered a fracture that is aged and partially healed.

The Kyphoplasty procedure can be described as follows: (1) insertion of a straight, sharp obturator and straight cannula assembly into the pedicle; (2) withdrawal of the blunt obturator leaving the cannula in place; (3) insertion of a drill, drill a channel, and withdraw of the drill; (4) insertion of an expandable structure (such as a balloon), expansion and contraction of the structure and then removal of the structure leaving a void; and (5) filling the void with cement or other substrate. The current Kyphoplasty protocols fail to allow control, which practitioners demand, over the void creation parameters.

In an effort to solve these problems, other inventions have sought to provide a transpedicular approach into the bone and then attempt to perpendicularly articulate after entering the interior bone. Such inventions have a number of unfavorable outcomes. First, inventions using a hinge to achieve articulation cannot be engaged because there is insufficient space to allow for the tool to articulate inside the bone. Many such inventions do not have a locking mechanism to allow partial articulation so that sufficient space for full engagement may be created. These supposed cavity creating tools only result in a tamping mechanism useful in extension of the cannula. The limited strength and space for articulation restrict these inventions from reaching an operational position. The current tools in the art do not contemplate a necessary curved configuration coupled with a fixed tip to effectuate the optimum result.

A need exists for a tool which can function in either a vertebroplasty, Kyphoplasty, or similar internal-bone treatment procedure, which will pass through a cannula or bone access tool and also allow immediate impact in axial or lateral directions. In order to optimize surgical procedures, an extrapedicular approach into the bone is needed. An ideal tool would create a critical curve gradient for approaching the bone in a unilateral manner.

A further need exists for a tool with sufficient tensile strength to allow a surgeon to freely prepare bone tissues for treatment. Prior inventions have sought to provide extraordinary safety features which would prevent injury to a patient if the tool became dislodged. The result has produced overengineered products that do not leave enough strength on the distal end to provide a tool that is strong enough to perform the desired function of preparing the bone for treatment. There is a need in the industry for a tool which possesses the strength to effectively prepare the bone tissue while retaining some flexibility and protecting a patient's health.

These disadvantages and shortcomings of the prior art are presented for the reader's understanding only. This disclosure is not meant to limit the present invention in any way. Other features and advantages of the present invention are set forth and will become apparent in the following description and drawings, as well as in the appended claims.

BRIEF SUMMARY OF INVENTION

The present invention calls for a hand-actuated, bone-preparation tool and bone access system for use in preparing the interior of a bone for therapeutic treatments. Predominantly, the tool will be used in procedures that call for a percutaneous approach into the bone. The present invention desirably permits surgeons an extrapedicular or transpedicular approach into vertebral bodies as they prepare that bone for treatment. Whether a transpedicular or extrapedicular approach is selected will depend on the patient's anatomy and the treatment sought. The bone access system of the present invention comprises a cannula and cannula introducer. The cannula has an interior lumen and both the cannula and introducer are curved. The introducer is threaded through the cannula lumen and is used as a cutting implement to guide and set the cannula before being retracted to expose the lumen. The cannula serves as the access sheath between the outside environment and the interior of a bone, through which a surgeon may introduce implements and prepare bone in a desirable manner as it is readied for treatment. The internal modifications of the bone are affected by the bone preparation tool according to the present invention. The tool is an elongated implement which comprises an ergonomic handle and a flexible rod which terminates in one of the specified bone preparation tips. The flexible rod is also curved to coordinate with the curved cannula. The tips and flexible rod are sized so that they may pass through the lumen of the cannula. While the cannula is rigid, the bone preparation tool including the tips and the rod are flexible. The tips according to the present invention are further described herein and include an off-set wedge, banana wedge, a pedestal tip, and a tapered tip.

It is a object of the present invention to allow a practitioner to prepare cancellous bone in a predictable and controlled manner. The present invention has as its objective the ability to achieve a transpedicular or extrapedicular approach without need for hinges or unpredictable locking mechanisms. An object of the present invention combination is to eliminate the need for a bilateral approach into the bone, by allowing a unilateral, midline approach toward the midline of the bone. As a further objective, the present invention seeks to minimize the need for additional space in a bone cavity to achieve a fully articulated position because its tips are fixed.

It is an object of the present invention to provide a tool to pass through a bone access tool and allow immediate movement in axial or lateral directions. It is a further object of the present invention to provide an ideal tool with the curve gradient between ten and thirty degrees (10°-30°. The present invention possesses the necessary curved configuration to make the tool operational for the stated purposes. It is an object of the present invention to employ an off-set wedge, a banana wedge and other tips which necessarily meet the needs of a surgeon to prepare tissue in its naturally occurring anatomical position not immediately accessible outside the cannula. It is another object of the present invention to compact cancellous bone in order to create a directionally controlled area in preparation for bone treatment. Desirably, the compaction and expansion prepares the bone within the vertebral body for therapy such as repair and reinforcement. Another object of the present invention is that it possess the strength to effectively prepare bone tissue while protecting a patient's health and safety. It is yet another object of the present invention to allow a surgeon to optimize application of bone void filler material and minimize damage to surrounding tissues.

The foregoing has outlined, in general, the physical aspects of the invention and serves as an aid to better understand the more complete detailed description which follows. In reference to such, there is to be a clear understanding that the present invention is not limited to the method or detail of construction, fabrication, material, or application of use described and illustrated herein. Any other variation of fabrication, use, or application should be considered apparent as an alternative embodiment of the present invention.

BRIEF DESCRIPTION OF THE DRAWINGS

The following drawings serve to illustrate the various aspects of the invention. These drawings further describe by illustration, the advantages and objects of the present invention. Each drawing is referenced by corresponding figure reference characters within the "DETAILED DESCRIPTION OF THE INVENTION" section to follow.

FIG. 8 is a top perspective view of the off-set wedge according to the present invention, while

The invention may be embodied in several forms without departing from its spirit or essential characteristics. The scope of the invention is disclosed below and will be further defined in the claims and in the specific description preceding them. All embodiments that fall within the meaning and range of equivalency of the claims are therefore intended to be embraced by the claims.

DETAILED DESCRIPTION OF INVENTION

The present invention allows a physician, surgeon, or medical professional (used interchangeably herein) to prepare a bone for treatment, predictably, and in a controlled manner. By employing the aspects of the present invention, a surgeon can access the interior of a bone and prepare a bone to receive treatment. The present invention gives a surgeon a tool with which to minimize damage to surrounding tissues but optimize preparation options. The bone preparation tips provided with the present invention meet the needs of the surgeon in preparing tissue by accessing its naturally occurring anatomical position. In the past, aspects of the bone and tissue surfaces that required treatment preparation were not immediately accessible outside the line of the cannula. While using minimally invasive procedures, the present invention allows a physician to treat tissue outside the radius or peripheral region of the cannula lumen which was previously inaccessible without deformable or articulating mechanisms. With the present invention, the peripheral regions become accessible while permitting the tip of the tool to remain fixed. The advantages of the bone preparation tool of the present invention allows surgeons to prepare bone in each of the unique ways described herein.

Although the disclosure hereof is detailed to enable those skilled in the art to practice the invention, the physical embodiments herein disclosed merely exemplify the invention that may be embodied in other specific structures. Although the preferred embodiment is described, the details may be changed without departing from the invention.

The systems and methods embodying this invention can be adapted for use virtually in any interior body region, particularly where the preparation of bone tissue is required for a therapeutic or diagnostic purpose. The preferred embodiments call for the invention to be used to treat vertebral bodies. This is because the tools and systems which embody the invention are well-suited for use in this environment. It should be appreciated that the invention features can be used in other interior body regions as well.

Figure 1:
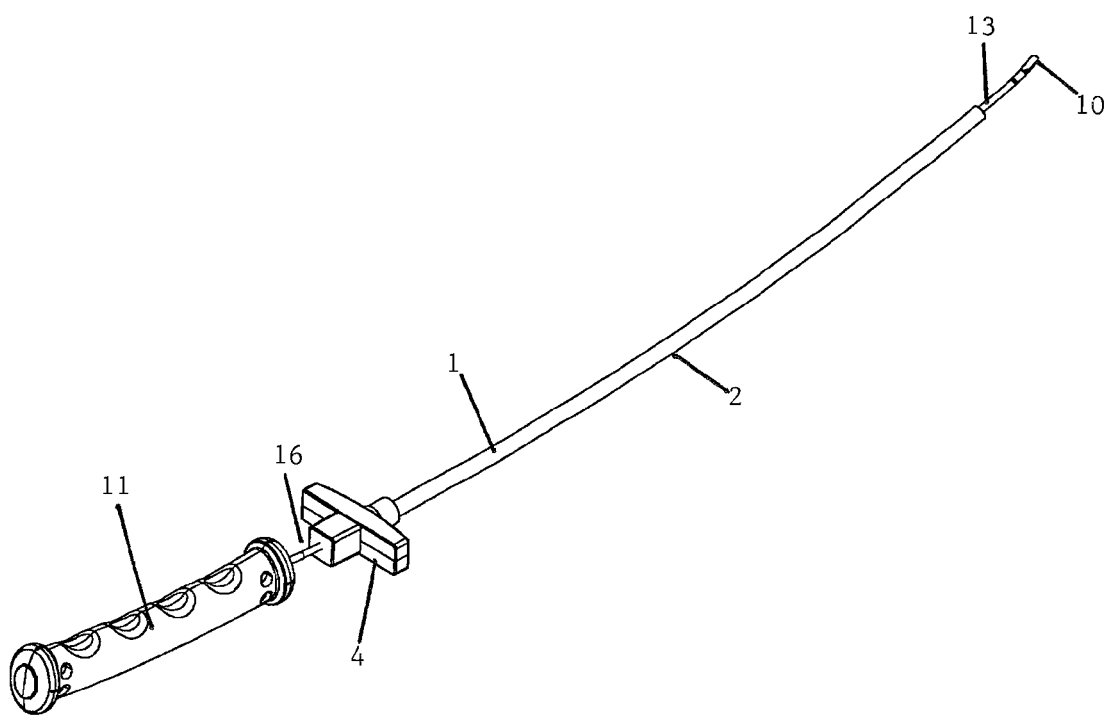
FIG. 1 is a rear perspective view of the bone preparation tool and cannula according to the present invention.
Figure 2:
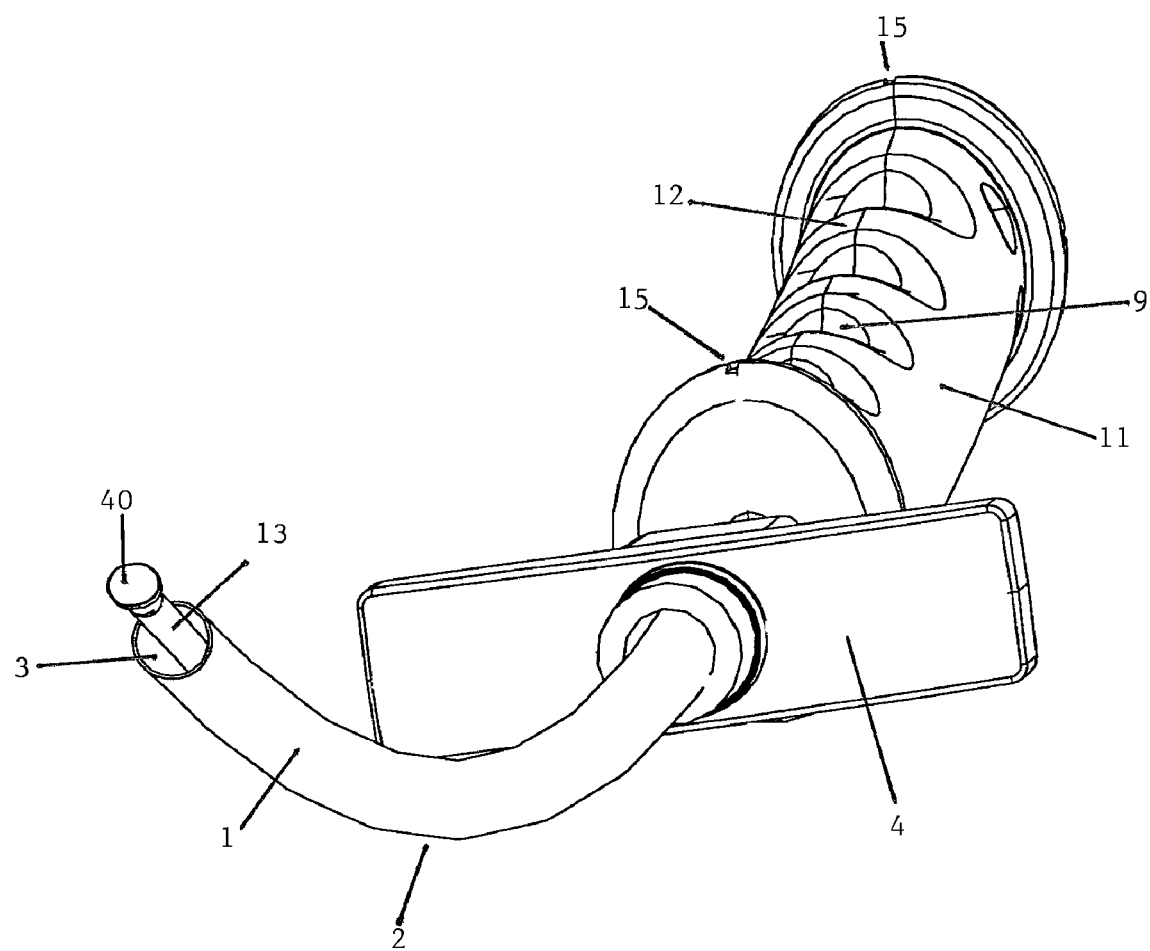
FIG. 2 is a front perspective view of the bone preparation tool with cannula according to the present invention.

A bone preparing tool according to the present invention is illustrated in FIGS. 1-2. This bone preparing tool is designed for specific use with the specialized bone access system according to the present invention. The bone access system of the present invention is shown in FIGS. 3-6. The tool and system, when used in conjunction, provide a percutaneous, transpedicular approach into the interior of a vertebral body for the purpose of preparing the bone for treatment and particularly to receive a therapeutic substance. As used herein treatment is used interchangeably with therapeutic substances or therapies and may also be referred to as bone filling material and may include substrates, medicines, bone cement, bone graft material, or bone growth factors, or other materials or similar treatment substances. Applications may further include insertion of expandable materials or larger tools for reshaping bone; deliverance of strengthening material; and anatomy restoration generally. The aspects of the present invention eliminate the need for a bilateral approach into the bone, but allow a unilateral approach toward the midline of the bone.

The present invention achieves a transpedicular approach without need for hinges or unpredictable locking mechanisms. Furthermore, the present invention does not require additional space to achieve a fully articulated position. The operational aspects are fixed. The present invention possesses the necessary curved configuration to make the tool operational for the stated purpose. Furthermore, the present invention possesses the strength and flexibility to effectively prepare the bone tissue while protecting a patient's health and safety.

The present invention is specifically described in the context of the treatment of human vertebrae. Of course, other human or animal bone types can be treated in the same or equivalent fashion. Aspects of the invention can be advantageously applied for diagnostic or therapeutic purposes in other areas of the body. By way of example, and not limitation, the present systems and methods may be used in any bone with a real or potential interior cavity, including the radius, the humerus, the vertebrae, the femur, the tibia, or the calcaneus.

In addition to the specific uses described herein, the bone preparation tool and bone access system described would also be well-suited for use in treating and/or reinforcing weakened, diseased and/or fractured bones in various locations throughout the body. For example, the disclosed tips could be used in conjunction with the delivery of therapies, such as cancer drugs, replacement bone cells, collagen, bone matrix, demineralized calcium, and other materials and/or medications, directly to a bone, thereby increasing the efficacy of the materials, reinforcing the weakened bone and speeding the healing process.

In a vertebroplasty or a Kyphoplasty, as described above, a cannula provides an access path into the bone. An obturator or trocar is used to access the interior bone location and set the cannula in place. Similarly, an access path and means to set the access path in place are required for the present invention. Not shown in the figures or described further is a spinal needle assembly that can be used for initially traversing soft tissue and muscle. As the prior art has demonstrated, the spinal needle assembly can be used to initially establish an access path through soft tissue and muscle and into bone such as a vertebral body. Herein, the necessary access is provided by the bone access system.

The bone access system of one embodiment of the present invention comprises a substantially round, rigid, tube-like cannula 1 which has a base 4, a curved shaft 2 and an interior lumen 3. The base 4 has a substantially rectangular configuration with a round void which joins with the lumen 3 to create a through-and-through lumen. The curved shaft 2 of the cannula abuts the base 4 and then extends from the base 4, located proximally on the cannula 1. The lumen 3 extends the length of the curved shaft 2. The cannula 1 is inserted into the vertebral body by a surgeon using a separate tool, which in this system is a curved, rigid, cannula introducer 5. The introducer 5 is an elongated cylinder with a proximal top portion 7 and a distal cutting surface 6. The introducer 5 aids in penetration of tissue by virtue of its cutting surface 6. The diameter of the elongated cylinder is only slightly less than the diameter of the interior lumen 3 of the cannula 1. Thus, it fills the cannula lumen 3 as the combination penetrates the tissues and until the surgeon is ready to proceed with a bone treatment procedure at which point he may retract the introducer 5.

The distal cutting surface 6 and a proximal top portion 7 of the introducer 5 have important respective functions. The cutting surface 6 allows penetration of tissues including soft tissue, muscle and bone. As stated, the cutting surface 6 is located at the distal end of the introducer, but it protrudes from the distal end of the cannula 1 when the two are conjoined. The cutting surface 6 of the introducer has a point and a plurality of cutting faces, which in conjunction with the introducer's rigidity, allow it to penetrate soft and hard tissues when force is applied to the top portion 7. The top portion 7 has a substantially flat surface and is oriented in a perpendicular manner with the proximal end of introducer's elongated cylinder. The introducer's top portion 7 has a diameter larger than the tube of the cannula as demonstrated in FIG. 6. This disparity in diameter is a desirable feature to facilitate the introduction of the cannula 1 into the tissue when force is applied to the introducer 5. After the cannula 1 is positioned, the top portion 7 is also used to aid in the retraction of the introducer 5.

With the cannula 1 in position, a rigid, interior passage is configured and adapted so that the flexible bone preparation tool may be inserted into the bone through the cylindrical, curved lumen 3 of the cannula 1. The bone preparation tool of the present invention is employed by passing the flexible rod 13 and bone preparation tip 10 through the cannula 1 of the bone access system. The features of the bone preparation tips 10, described below, allow immediate movement in axial or lateral directions after traversing the cannula and entering the bone with a transpedicular or extrapedicular approach. It is preferred that the cylindrical interior lumen 3 of the cannula 1 allows the bone preparing tool to be freely rotatable in all directions including but not limited to axial, lateral, posterior, and anterior. In an alternative embodiment, the cannula 1 or the bone preparing tool, or both, may be designed to impose a limited range of rotation. For instance, the cannula 1 may have stops that allow the bone preparing tool to be rotated within a certain range, but no further. In one variation of this embodiment, the limited range of rotation may be adjustable so that the range of rotation may be selected by the surgeon either before or during the surgical procedure. At a minimum, a visible notch 15 provides an indication to the surgeon of the tool curve orientation because the notch is aligned with the curve of the rod. Such a notch 15 is shown in FIG. 2.

The bone preparing tool comprises a ergonomic handle assembly 11, a flexible rod 13, and a bone preparation tip 10 at the distal end of the flexible rod 13. The tool is meant to driven by a surgeon's hand. The ergonomic handle assembly 11 abuts the proximal end of the flexible rod 13. The flexible rod 13 is substantially cylindrical in configuration with a curve complementary to the curved shaft 2 of the cannula. The preferred gradient angle of the cannula and flexible rod curve is fifteen degrees (15°). The angle may range between ten and thirty degrees (10°-30°). Any angle within this range will provide the desired functionality and results which is to affect a unilateral, and extrapedicular or transpedicular approach into the bone. The cylinder of the flexible rod 13 has a diameter smaller than that of the lumen 3 of the cannula 1. The flexible rod 13 includes laser hash marks 16 shown on FIG. 1 to provide depth indicators as a visual cue for the depth of the flexible rod in the working cannula 1. The flexible rod 13 terminates distally in a bone preparation tip 10. Depending on the desired bone treatment, the surgeon may choose from an off-set wedge 20, a banana wedge 30, a tapered tip 40, or a pedestal tip 50 for preparing a bone.

Figure 3:
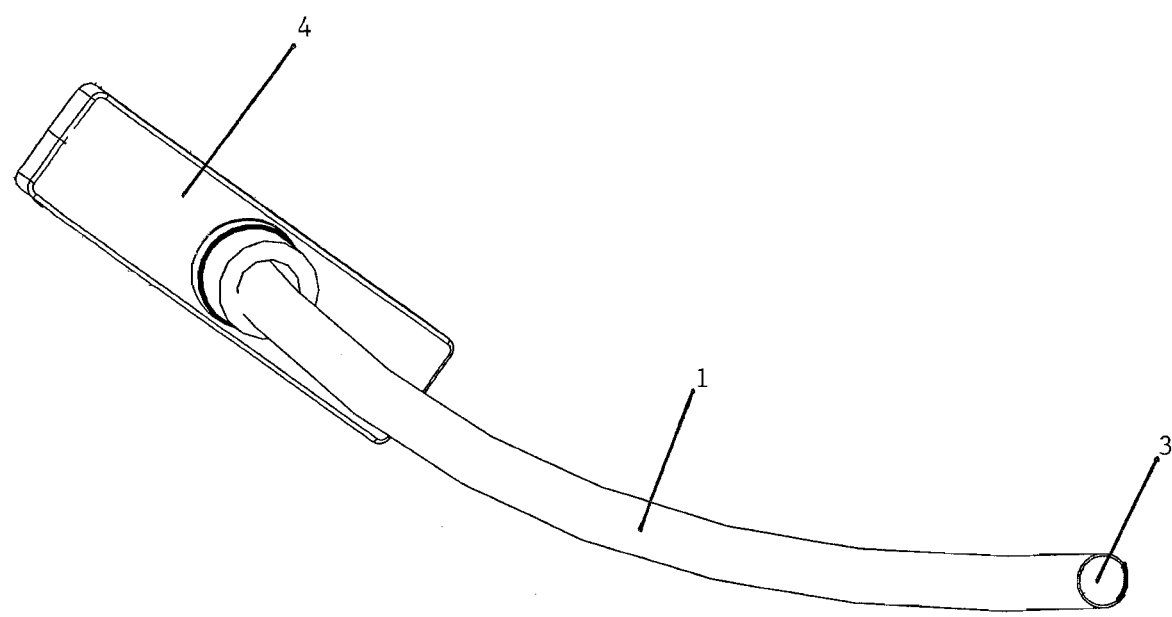
FIG. 3 is a perspective view of the cannula according to the present invention.
Figure 4:
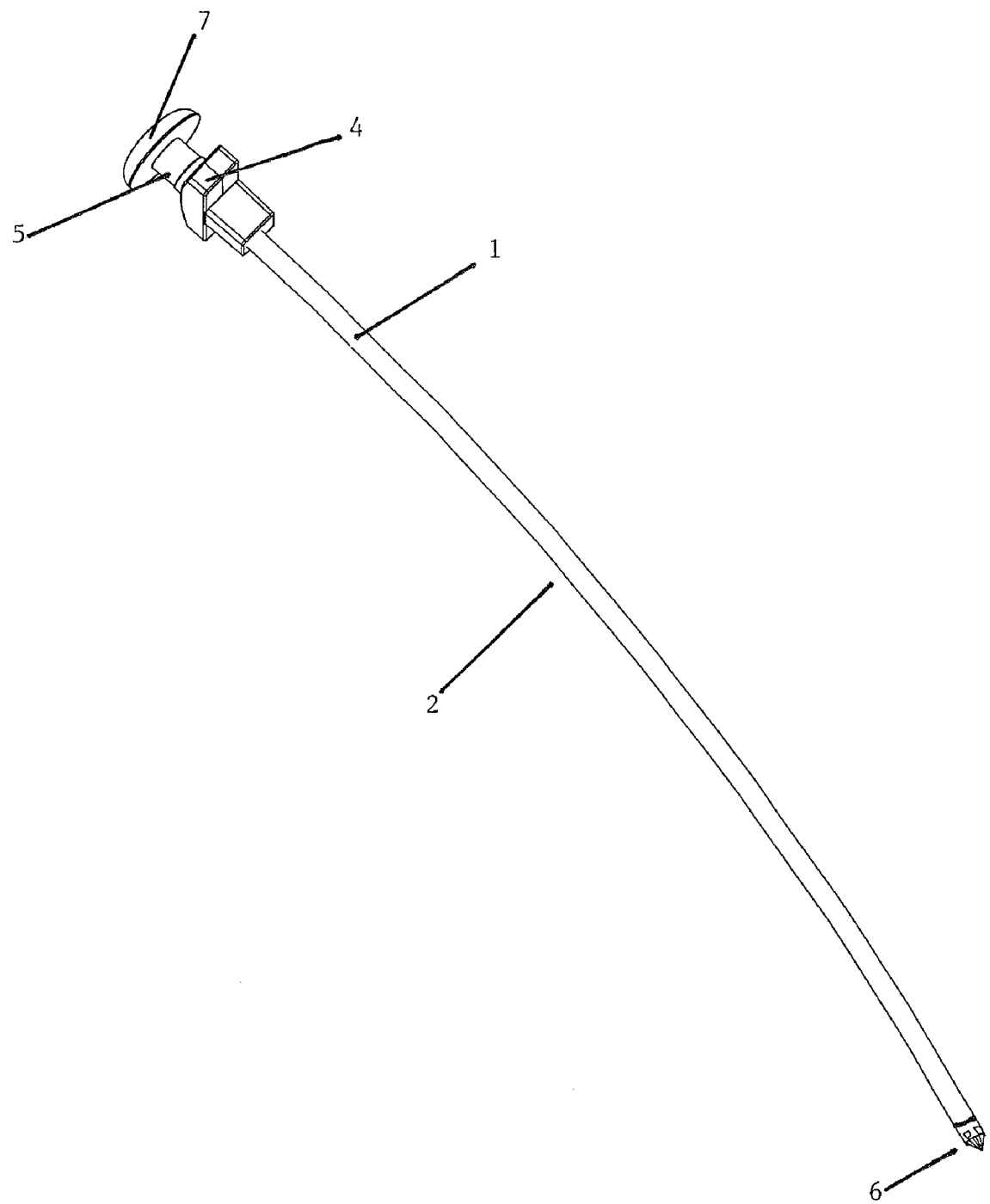
FIG. 4 is a perspective view of the introducer and cannula according to the present invention.
Figure 5:
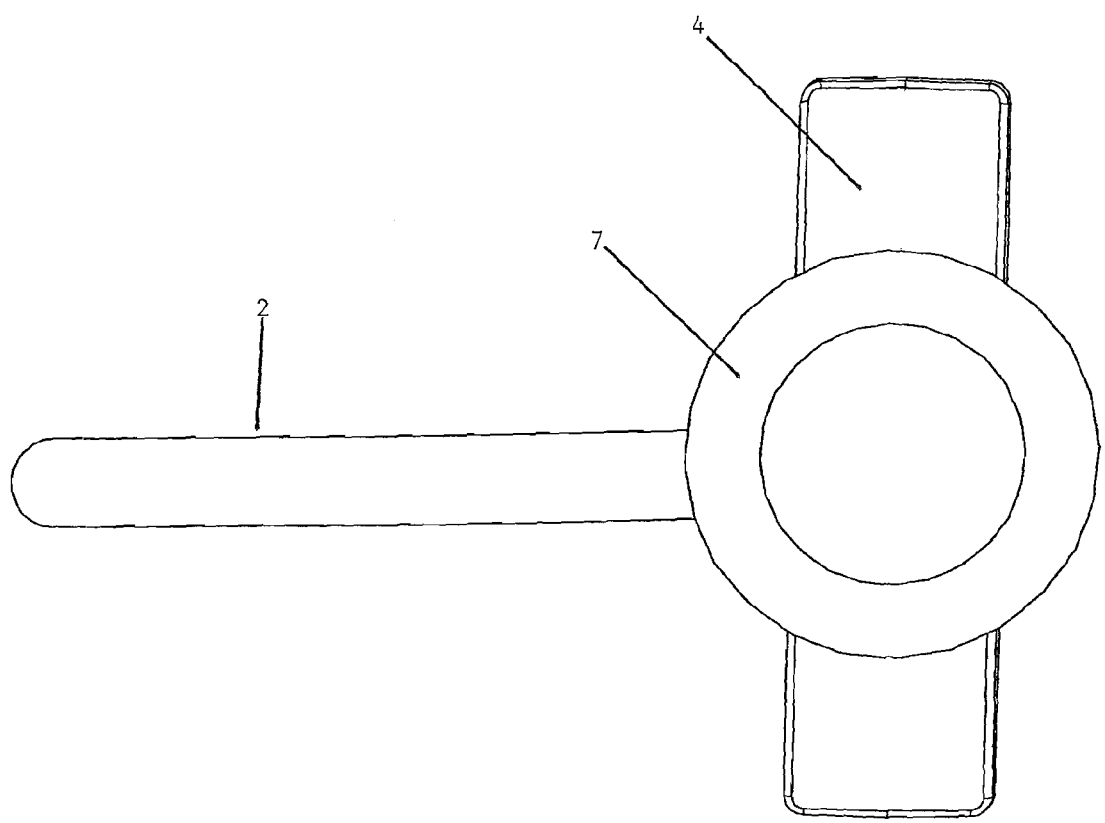
FIG. 5 is a top view of the introducer and cannula according to the present invention.
Figure 6:
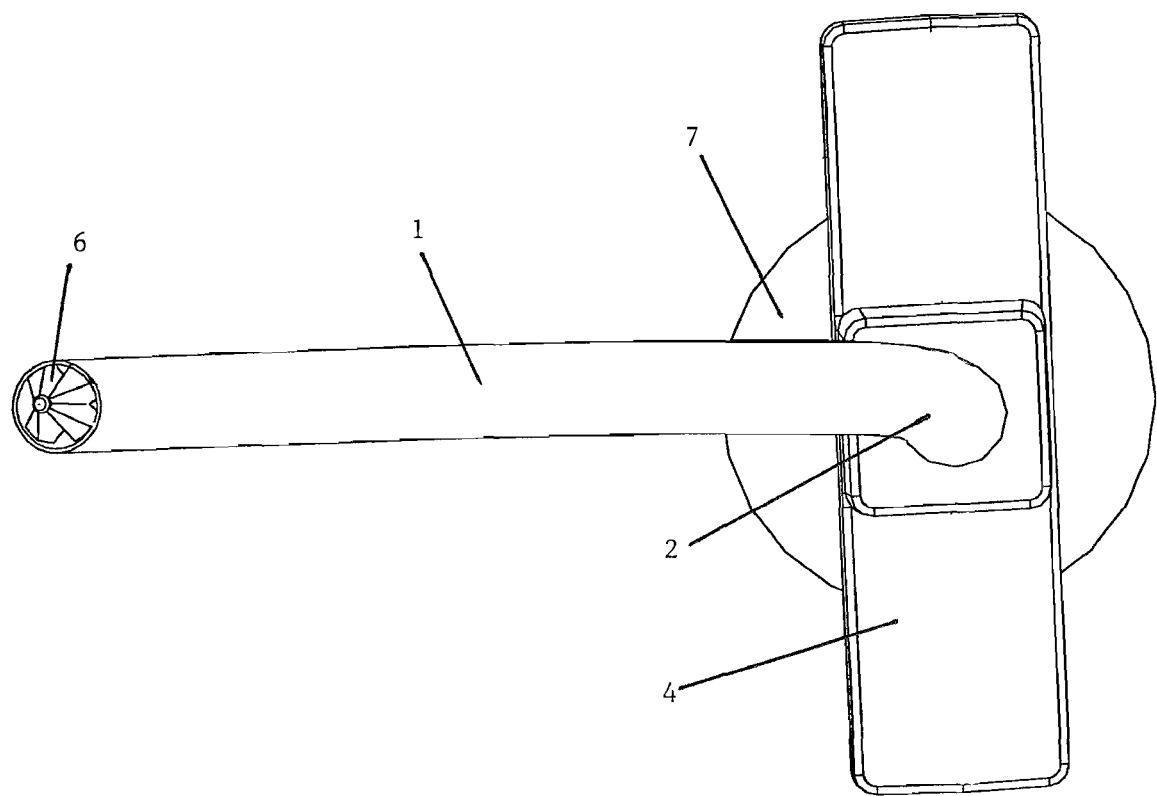
FIG. 6 is a bottom view of the introducer and cannula according to the present invention.

FIG. 1 demonstrates the curved ergonomic handle assembly 11. In this figure, a bone preparation tip 10 is attached at the end of the flexible rod 13. The combination of the flexible rod 13 and the bone preparation tip 10 passes through the curved cannula 1 until the bone preparation tip 10 protrudes from the distal end of the cannula 1 and into the bone to be treated. An example of the cannula 1 is shown in FIG. 3. As an important feature of the cannula 1, a base 4 is provided near the proximal end of the cannula to aid in the placement and later removal of the cannula. The composite of FIGS. 7-14 show representative bone preparation tips according to the present invention, each having utility in preparing a bone for treatment.

FIG. 2 is a front perspective view of the ergonomic handle assembly 11 with the flexible rod 13 attached. The ergonomic handle assembly 11 has a unique, ergonomic design that provides unique maneuverability to the surgeon during use. The ergonomic handle assembly 11 helps provide a better grip and greater control of the bone preparation tips during initial positioning of the tips and the bone preparation that follows. The finger holds 9 of the grip 12 allow secure and predictable reaction of the bone preparation tool in the surgeon's hand. The shape and bend of the handle ergonomically compliment the angle of the surgeon's hand and his critical movements during the bone preparation process.

Figure 12:
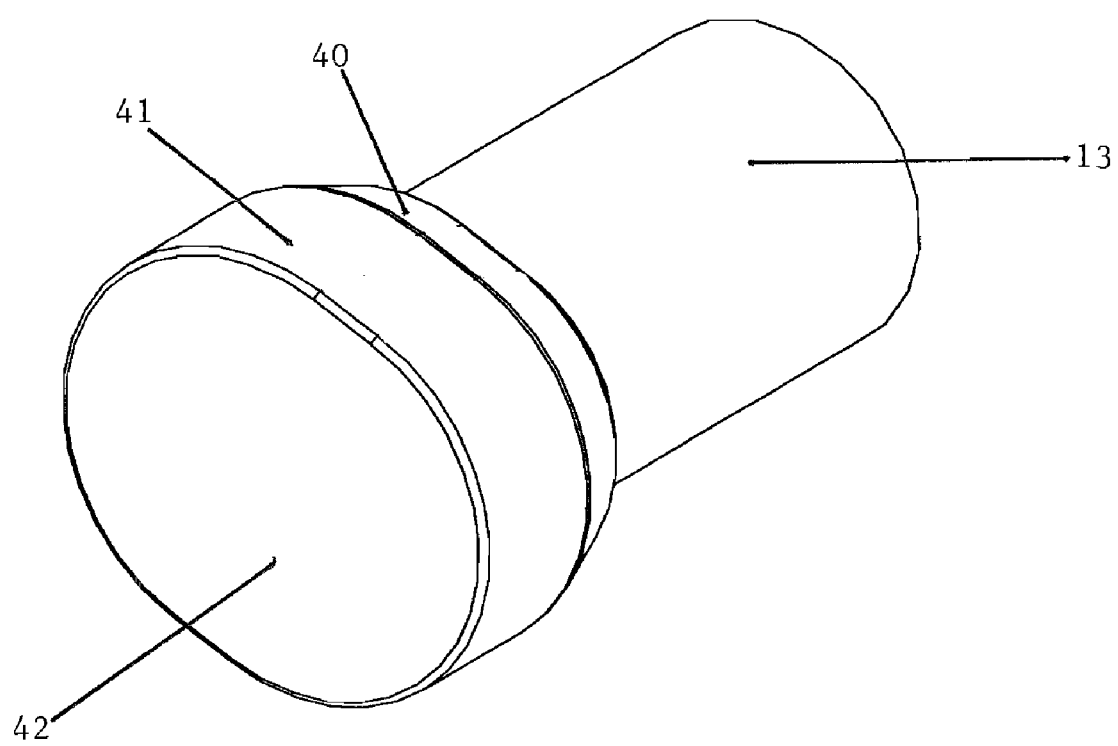
FIG. 12 is a front perspective view of the pedestal tip according to the present invention.
Figure 13:
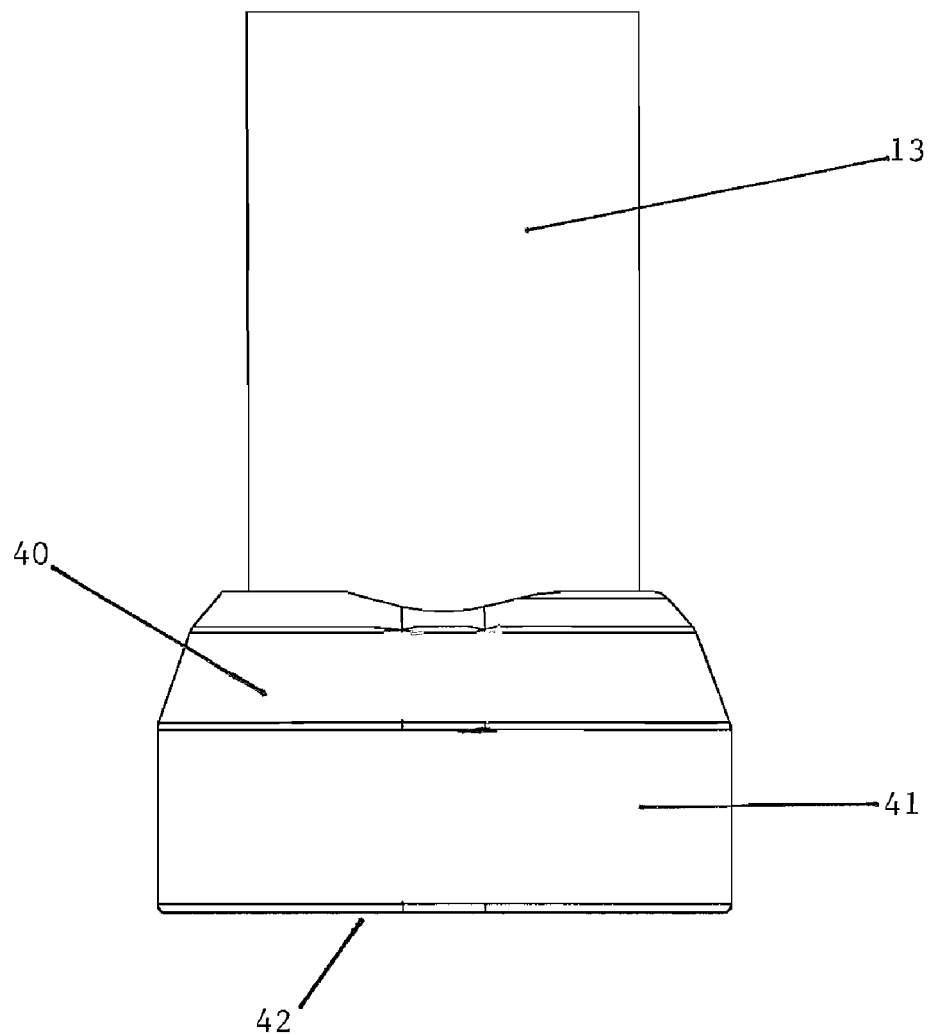
FIG. 13 is a side plan view of the pedestal tip according to the present invention.

The cannula 1 and cannula base 4 obscure a great deal of the flexible rod 13 from view in FIG. 2. The flexible rod 13 is shown protruding from the lumen 3 of the curved shaft 2 of the cannula 1. The bone preparation tip 10 illustrated in FIG. 2 is the pedestal tip 40 which is shown in FIGS. 12 and 13 and is further described below. An important feature for the surgeon using the bone preparation tool is illustrated in FIG. 2. This feature is the notch 15 provided on the handle as a point of reference for the angle of the flexible rod 13 and thus the bone preparation tip 10 protruding from the end of the cannula 1 and out of view from the surgeon.

FIG. 2 illustrates the curved nature of the ergonomic handle assembly 11 and the flexible rod 13 for optimum access to the bone. The ergonomic handle assembly 11 and flexible rod 13 combination, when coupled with the cannula 1 of FIG. 3, possess the necessary curved configuration to make the tool operational for the stated purposes including a transpedicular or extrapedicular approach to the bone without need for hinges, undesirably large access systems, etc. The cannula 1 may be used to deliver a therapeutic substance into the bone after it is prepared to received the treatment with the bone preparation tool.

Once again, the pedestal tip 40 (detailed further below and in FIGS. 12 and 13) is represented in FIG. 2. Any tips disclosed and claimed may be connected at the distal end of the flexible rod or they may be connected to individual flexible rods which may then be assembled with an ergonomic handle assembly 11. As yet another alternative, the ergonomic handle assembly, flexible rod, and respective bone preparation tip may be single units of a kit or as selected by a surgeon. In a preferred embodiment, the flexible rod 13 has an off-set wedge 20 that provides a strong, fixed, and angled or sloping surfaces as described below.

The bone preparing tool of the present invention becomes critical after access to the interior bone is achieved. The flexible rod and bone preparation tips, which are inserted through the cannula 1, must be and are suited to the surgeon's needs for preparing the bone for treatment.

The first bone preparing tip demonstrated in FIGS. 7, 8, 8a, and 9, is the off-set wedge. The off-set wedge comprises a dual cutting edge 21 which is set off from the midline of the flexible rod. A flat bottom edge 25 extends in near parallel orientation with and from the flexible rod until it adjoins a leading edge 24 of the tip. The leading edge should be nearly perpendicular to the flat bottom edge 25 and the flexible rod 13. Side walls 26 connect the flat bottom edge 25 to the leading edge 24 and the dual cutting edge 21. The side walls 26 of the tip are beveled to complement and contour to the other faces which they join. The dual cutting edge 21 and flat bottom edge 25 occur on opposing sides of the beveled side walls 26.

Turning now with more particularity to the dual cutting edge of the off-set wedge, the dual cutting edge 21 extend tangentially from a common point near the flexible rod. The space created between the parting dual cutting edges is interposed by a connecting face 22 at the upper-most cutting surfaces. It is anticipated that the angle between the dual cutting edges could be negligible, thus eliminating the need for the connecting face 22. In the preferred embodiment and referring to FIG. 7, the dual cutting edge flares to an apex over a gradual grade 23. The grade descends to adjoin a wedge which is the leading edge 24 of the tip. It is not necessary that the off-set wedge include any gradient, but could form an abrupt ninety-degree angle with the flexible rod. Other angles are anticipated as having specialized function.

The off-set wedge specializes in cutting peripherally to the side of the cannula's diameter. This device is ideal for coring, wedging, or pushing away bone. The off-set wedge 20 may function to compress cancellous bone, but it may also help to elevate cortical bone to an anatomic position. The physician turns or spins the off-set wedge 20 and then advances it. By repeating these steps the physician is able to prepare the bone by evacuating a cylindrical shape in a bone. Because the cylindrical shape can extend axially and laterally beyond the confines of the cannula, the off-set wedge 20 is able to enhance preparation of a bone for treatment.

Figure 7:
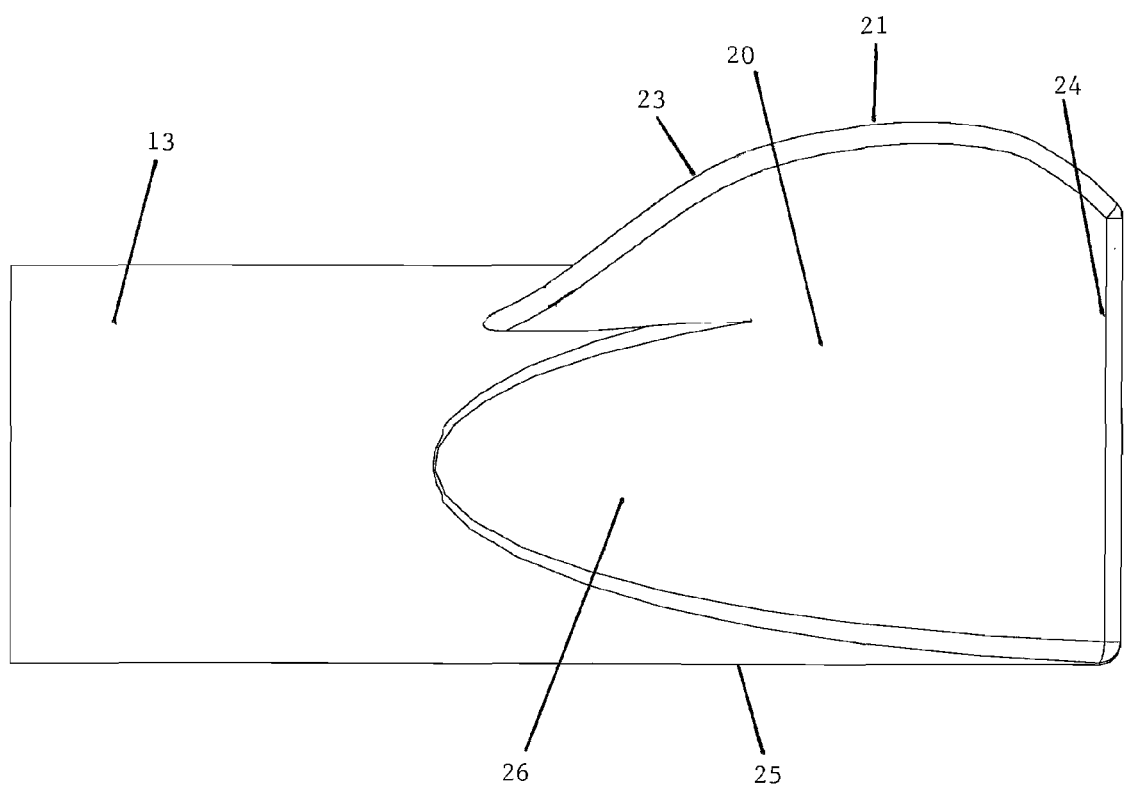
FIG. 7 is a side plan view of the off-set wedge according to the present invention.
Figure 8:
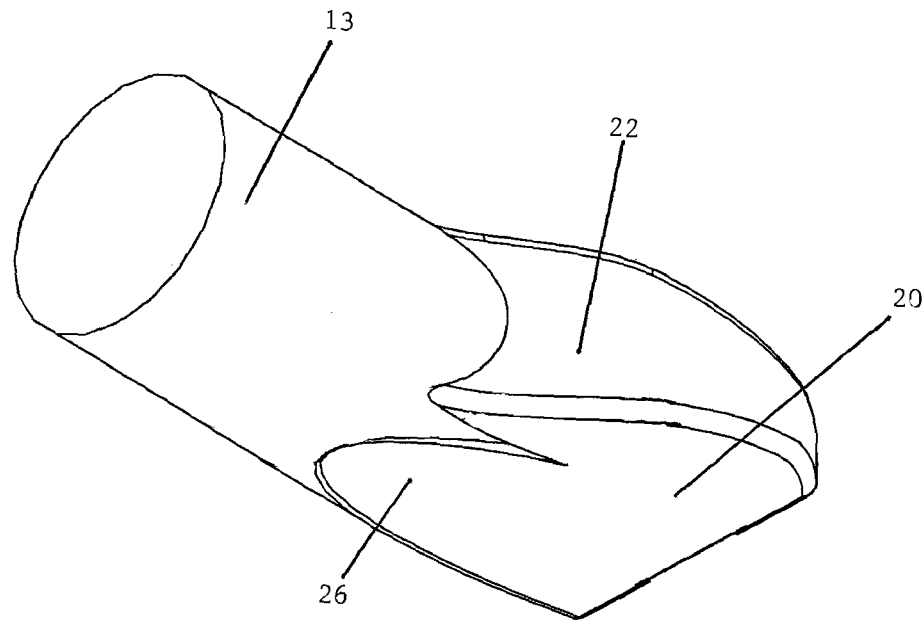
Figure 9:
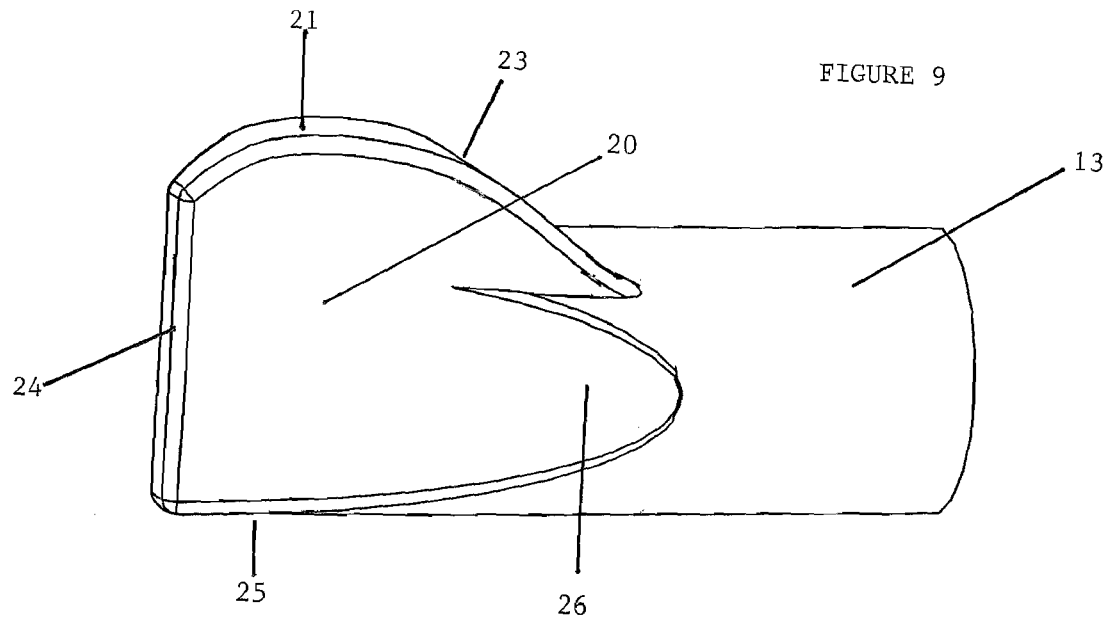
FIG. 9 is a perspective view of the side and front of the off-set wedge according to the present invention.
Figure 8A:
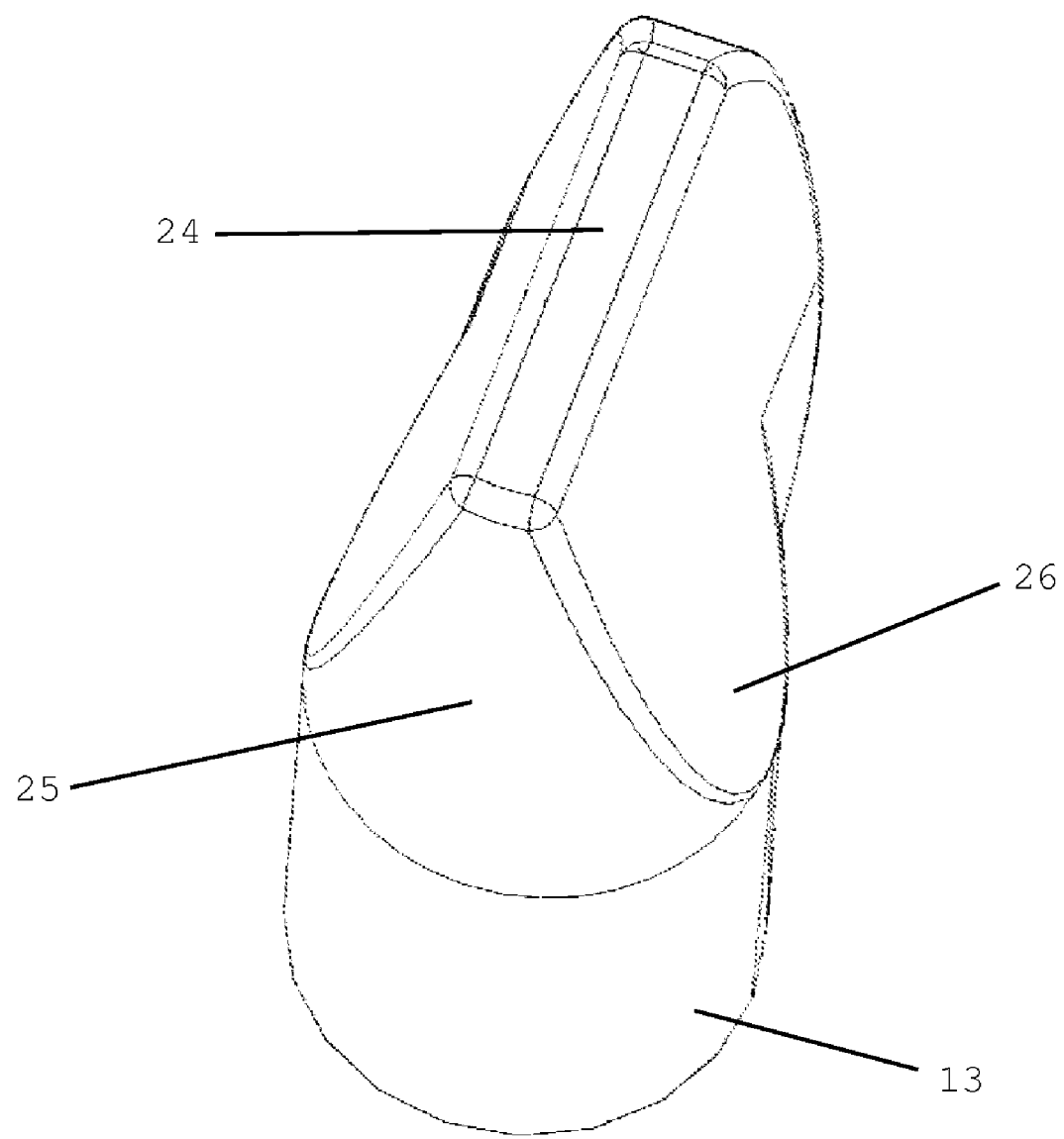
FIG. 8*a* is a bottom perspective view of the off-set wedge tip.

FIG. 7 presents a side view of the off-set wedge 20 according to the present invention. The off-set wedge 20 is further illustrated in FIGS. 8, 8a, and 9. This particular aspect of the present invention lends itself uniquely to the objectives set forth herein. The off-set wedge 20 allows a transpedicular approach to the bone without need for hinges or unpredictable locking mechanisms anywhere in the system. The off-set wedge 20 also does not require additional space to achieve an articulated position. It is fixed at a set angle. These unique features of the fixed, non-moving bone preparation tip coupled with a transpedicular approach permits the instrument to have the tensile strength necessary to effectively prepare the bone tissue while protecting a patient's health and safety.

Figure 10:
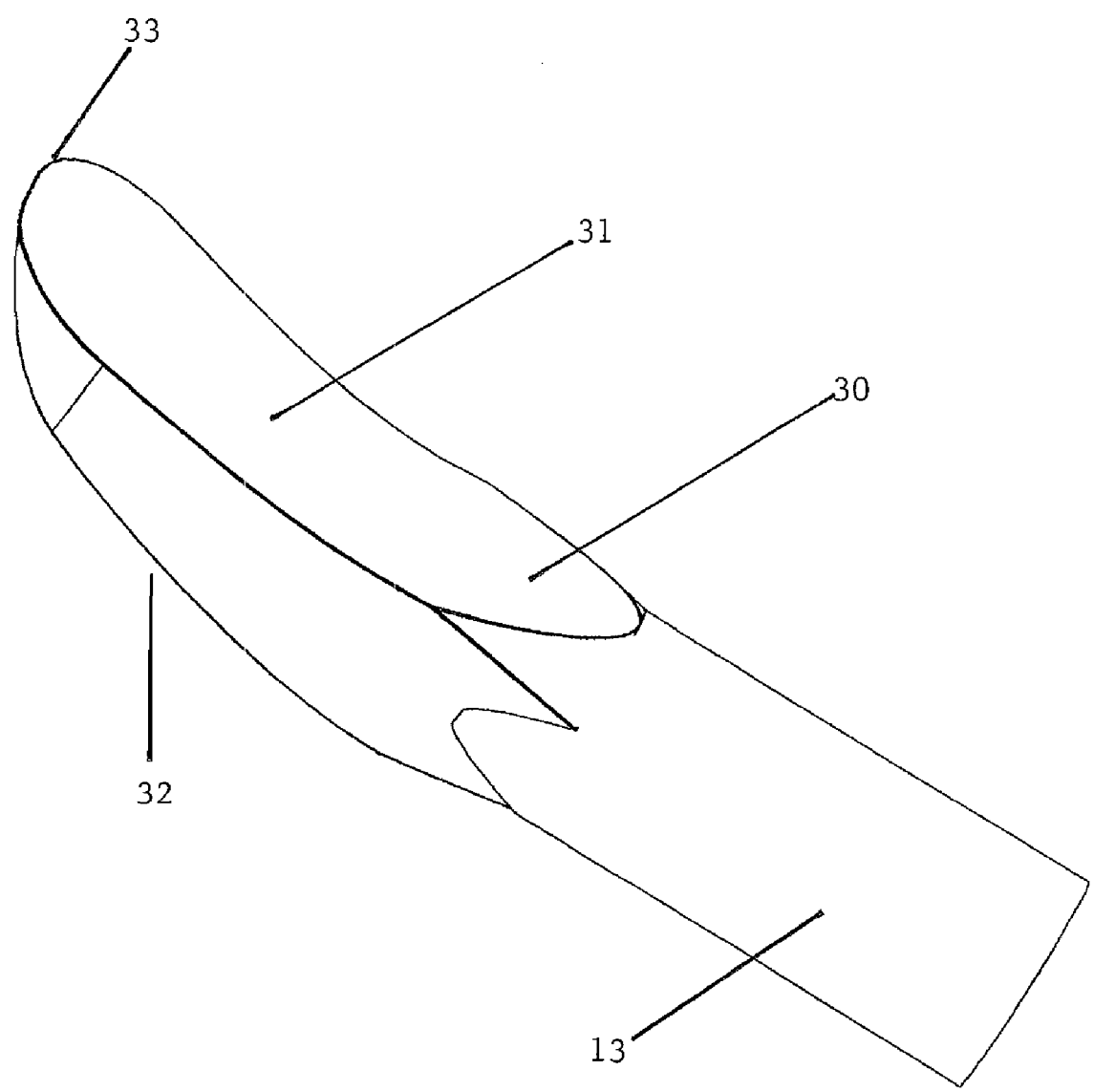
FIG. 10 perspective view of the banana wedge according to the present invention.
Figure 11:
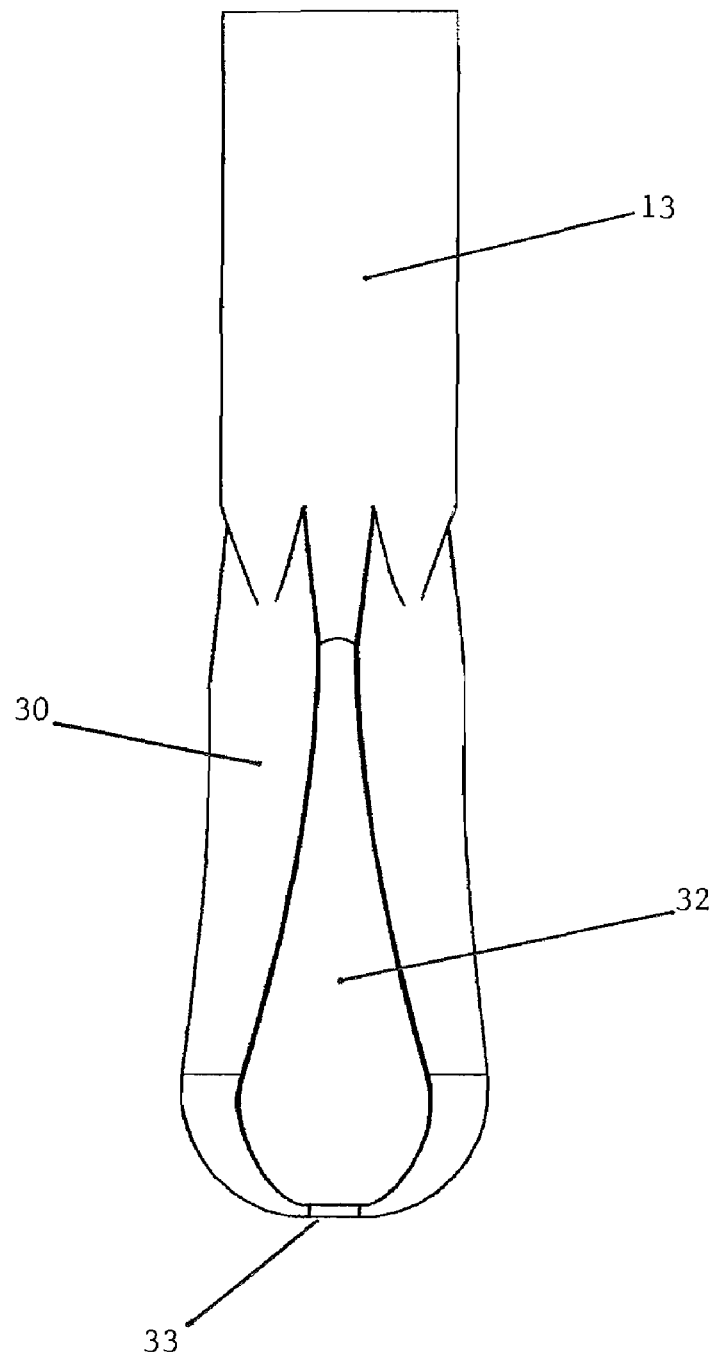
FIG. 11 bottom plan view of the banana wedge according to the present invention.

The banana wedge is illustrated in FIG. 10 in perspective view and has unique utility in bone preparation. This bone preparation tip provides a directional cutter. It is used to carve, scrape, and cut bone in one direction. The unique shape of the banana wedge provides specialized function. The first face is concave. The face opposite of the concave face 31 is convex. The convex face 32 provides a smooth surface which will guide the tip but will not penetrate outer bone areas which must be protected from puncture. The concave face 31 and the convex face 32 intersect to create a sharp cutting chisel ledge 33 to aid the practitioner in bone preparation. This sloping, sharp tool is ideal for preparing areas of bone which are harder and denser. The chiseled nature of the banana wedge 30 is evident in FIGS. 10 and 11. FIG. 10 demonstrates the banana wedge from a perspective view. The convex face 32 is more apparent in FIG. 11 where the view is given from the bottom of this tip. This view demonstrates the re-enforcement bevels which are one acceptable manner to strengthen the tip for its application. The narrowing from the operational faces of the banana wedge to the flexible rod 13 are apparent in these Figures.

Figure 14:
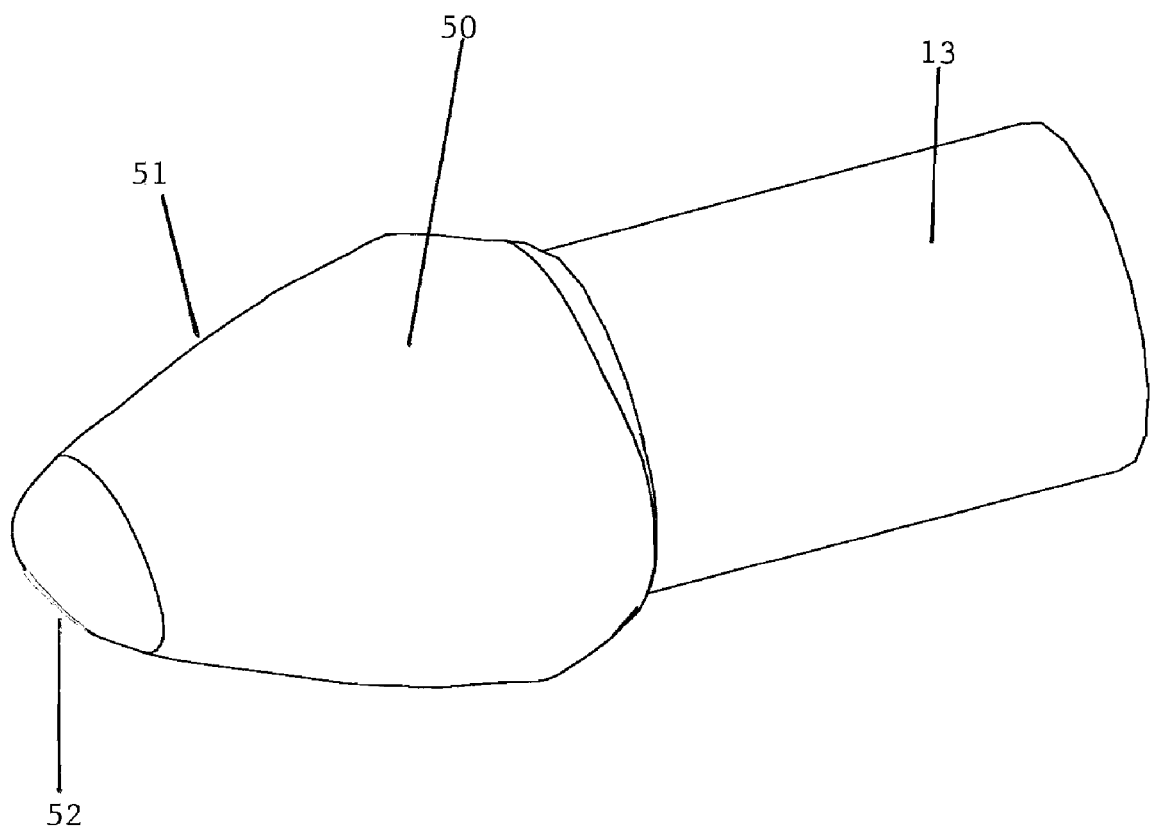
FIG. 14 is a perspective side view of the tapered tip according to the present invention.

The next bone preparation tip is the tapered tip. FIG. 14 shows the tapered tip 50 in perspective view. The tapered tip 20 has specific engineering which allows its surface to be more curved and less sharp. The tapered tip provides a sloping face 51 which terminates in a point 52. However, the point is not sharp thus preventing undesirable penetration through the end of the bone. Herein the point may be referred to as non-penetrating. This tapered tip 50 enables a practitioner to channel forward during bone preparation. It is a bone tunneling device which creates a forward channel. This particular bone preparation tip 50 has highly specialized and critical functionality in bone treatment cases. It is likely the initial device to be utilized out of the cannula in order to prepare the initial channel for the other tips to enter and achieve their respective functionality.

FIG. 12 illustrates a perspective view of the pedestal tip 40. The pedestal tip 40 is used to push bone and treatment substances. The pedestal tip 40 comprises a substantially flat, ovoid or round, pushing surface with a diameter at or near that of the cannula lumen 3. The flat pushing surface 42 transitions abruptly and nearly perpendicularly to a trunk 41 which extends laterally toward the flexible rod until narrowing to meet the flexible rod 13 which has a smaller diameter than that of the flat pushing surface. The side view (FIG. 13) of the pedestal tip 40 illustrates the flat surface 42 ideal for the pushing required of the pedestal tip 40.

The pushing functionality of the pedestal tip compresses and compacts bone and other materials. This pedestal tip 40 functions to urge residual bone filling material into the bone. The pedestal tip 40 is also instrumental within the cannula and the bone prepared for treatment as it aids in pushing therapeutic substrates through the cannula and into the desired passages of the bone as prepared by a practitioner. The cannula 1 is also important where a treatment substrate or bone graft material is injected into the bone. A bone-cement filling device can function to deliver a bone filling material into an interior bone but is not shown or claimed. Alternatively, a syringe can be used for delivering the bone filling material to the cannula and the pedestal tip 40 will push it through. The therapeutic substances have the potential to leak out of the bone and contaminate surrounding tissue. Because the surgical tools access the vertebral body through the opening formed in the cortical wall and are confined by the cannula 1, the therapeutic substances are contained until absorbed, hardened, or the protocol is otherwise completed. The bone treatment procedure is closed by withdrawing the bone preparing tool and cannula from the targeted interior cavity and then from the outer body of the bone and outer tissues.

In a preferred embodiment, the bone preparing tool, including the ergonomic handle assembly 11, curved rod 13, and the respective bone preparation tip 20, 30, 40, or 50 is disposable. The ergonomic handle assembly 11 is desirably disposable and may be designed to be disposed of after completion of each surgical procedure. For instance, the ergonomic handle assembly 11 may be fabricated from low cost polymer material, have a simplified attachment mechanism, or both. This makes replacement of the disposable ergonomic handle assembly 11 relatively inexpensive. In one embodiment, the disposable ergonomic handle assembly 11 is made from plastic material. As an additional advantage of this embodiment, the plastic is radiolucent to reduce interference and benefit the surgeon with a better view of the treatment area. Alternatively, the entire bone preparation tool, or any components thereof, may be manufactured for sterilization and irradiation after one or more uses.

Manufacturing advantages may favor manufacturing the ergonomic handle assembly 11 in two pieces to be bound around the proximal end of the flexible rods 13. As a further alternative of assembling the present invention, the bone preparation tips and flexible rod will be permanently affixed to a separate disposable ergonomic handle assembly. An embodiment is contemplated to provide a kit of the bone preparation tips 10 and flexible rod 13 to be removably attached to the ergonomic handle assembly 11 by an attachment means. Fabrication of the bone preparation tool and bone access system components may be by machining, molding, or any other method.

Various embodiments of bone preparation tips are described in detail. In each case their sizes and shapes could be suited to the tissue being prepared for treatment. The bone preparation tool possesses the strength to effectively prepare the bone tissue while retaining some flexibility and protecting a patient's health. In addition to the preferred materials, the tool could be made of any bio-compatible metal (including, but not limited to, stainless steel, titanium, titanium alloys, tantalum, aluminum, aluminum alloys, or other metals) that has adequate shear and tensile strength to perform their function. Plastic polymers having suitable biomechanical properties may also be used for these tools. Alternatively, the tool may be plated or coated with a biocompatible material.

Other embodiments and uses of the invention will be apparent to those skilled in the art from consideration of the specification and practice of the invention disclosed herein. As will be easily understood by those of ordinary skill in the art, variations and modifications of each of the disclosed embodiments can be easily made within the scope of this invention as defined herein.

I claim:

1. A hand-actuated, bone preparation tool and bone access system for use in a percutaneous, extrapedicular approach to accessing the interior of a bone for the purpose of preparing a bone for treatment wherein the bone access system comprises:
   a cannula having a proximal base and a substantially round, tube-like, curved shaft with an interior lumen,
   the base having a substantially rectangular configuration,
   the curved shaft abutting and extending from the base,
   the base having a substantially round void adjoining with the lumen,
   the lumen extending the length of the curved shaft;
   a rigid, cannula introducer having a solid, elongated cylinder,
   the elongated cylinder having a diameter less than the diameter of the interior lumen of the cannula,
   the elongated cylinder terminating distally in a cutting surface,
   the cutting surface having a point and plurality of cutting faces for penetrating the soft tissues, muscles, and bone of a patient and allowing the physician to set the cannula,
   the cutting faces having a peripheral diameter less than but nearly equal to the diameter of the lumen such that it fills the lumen but may be retracted through the lumen,
   the elongated cylinder of introducer and cutting surface having a length longer than the cannula such that the cutting surface protrudes from the interior lumen of the cannula,
   wherein the introducer further comprises a top portion,
   the top portion being located on the proximal end of the cylinder,
   the top portion having a diameter larger than the elongated cylinder of the introducer,
   the top portion further having a diameter larger than the diameter of the cannula,
   the top portion has a substantially flat surface oriented perpendicularly to the cylinder of the introducer;
   and the bone preparation tool comprises:
   an ergonomic handle assembly,
   a flexible rod having a substantially cylindrical configuration with a curve complementary to the curved shaft of the cannula,
   the flexible rod further having a diameter smaller than the diameter of the lumen;
   the ergonomic handle assembly abutting the proximal end of the flexible rod; and
   the flexible rod terminating distally in a bone preparation tip, wherein the bone preparing tip further comprises:
   a flat bottom side substantially in the shape of a plane triangle, the flat bottom side shares a longitudinal axis with the rod,
   a leading edge is set at a substantially right angle intersecting the plane triangle,
   the leading edge forms a wedge axis for the bone preparing tip substantially shaped as a modified wedge having an off-set cutting blade,
   the cutting blades having a width less than the radius of the lumen,
   the rod having a radius less than the width of the cutting blades,
   the width of the blades and the radius of the rod set at two distinct points relative to and set apart from one another on a horizontal axis.

2. A tool as described in claim 1 wherein the bone preparation tip affects bone positioned laterally from of the lumen shaft.

3. A hand-actuated, bone preparation tool and bone access system for use in a percutaneous, extrapedicular approach to accessing the interior of a bone for the purpose of preparing a bone for treatment wherein the bone access system comprises:
   a cannula having a proximal base and a substantially round, tube-like, curved shaft with an interior lumen, the base having a substantially rectangular configuration,
the curved shaft abutting and extending from the base,
the base having a substantially round void adjoining with the lumen,
the lumen extending the length of the curved shaft;
a rigid, cannula introducer having a solid, elongated cylinder,
the elongated cylinder having a diameter less than the diameter of the interior lumen of the cannula,
the elongated cylinder terminating distally in a cutting surface,
the cutting surface having a point and plurality of cutting faces for penetrating the soft tissues, muscles, and bone of a patient and allowing the physician to set the cannula,
the cutting faces having a peripheral diameter less than but nearly equal to the diameter of the lumen such that it fills the lumen but may be retracted through the lumen,
the elongated cylinder of introducer and cutting surface having a length longer than the cannula such that the cutting surface protrudes from the interior lumen of the cannula,
wherein the introducer further comprises a top portion,
the top portion being located on the proximal end of the cylinder,
the top portion having a diameter larger than the elongated cylinder of the introducer,
the top portion further having a diameter larger than the diameter of the cannula,
the top portion has a substantially flat surface oriented perpendicularly to the cylinder of the introducer;
and the bone preparation tool comprises:
an ergonomic handle assembly,
a flexible rod having a substantially cylindrical configuration with a curve complementary to the curved shaft of the cannula,
the flexible rod further having a diameter smaller than the diameter of the lumen;
the ergonomic handle assembly abutting the proximal end of the flexible rod; and
the flexible rod terminating distally in a bone preparation tip, wherein the bone preparing tip further comprises:
a flat bottom side substantially in the shape of a plane triangle,
the flat bottom side shares a longitudinal axis with the rod,
a leading edge having a first end and a second end is set at a substantially right angle and intersects the plane triangle at the first end,
the second end of the leading edge intersects a concave triangle side, the concave triangle side disposed opposite the plane triangle,
the leading edge forms a wedge axis for the bone preparing tip substantially shaped as a modified wedge,
two side walls form two polygonal sides of the modified wedge and a third polygonal side of the modified wedge is affixed to the rod,
the two side walls share a first edge with the plane triangle,
the two side walls share a second edge with the leading edge of the tip,
a third edge of the side walls tapers from the rod,
dual, off-set cutting blades form the edges of the concave triangle side, the dual, offset cutting blades also form a fourth edge of the side walls and are shaped substantially in the shape of a solid arch,
the arch of the cutting blades having a radius less than the radius of the lumen,
the rod having a radius less than the arch of the cutting blades,
the radius of the blades and the radius of the rod set at two distinct points relative to and separated from one another on a horizontal axis.

4. A tool as described in claim 3 wherein the bone preparation tip affects bone positioned laterally from of the lumen shaft.

5. A hand-actuated, bone preparation tool and bone access system for use in a percutaneous, extrapedicular approach to accessing the interior of a bone for the purpose of preparing a bone for treatment wherein the bone access system comprises:
a cannula having a proximal base and a substantially round, tube-like, curved shaft with an interior lumen,
the base having a substantially rectangular configuration,
the curved shaft abutting and extending from the base,
the base having a substantially round void adjoining with the lumen,
the lumen extending the length of the curved shaft;
a rigid, cannula introducer having a solid, elongated cylinder,
the elongated cylinder having a diameter less than the diameter of the interior lumen of the cannula,
the elongated cylinder terminating distally in a cutting surface,
the cutting surface having a point and plurality of cutting faces for penetrating the soft tissues, muscles, and bone of a patient and allowing the physician to set the cannula,
the cutting faces having a peripheral diameter less than but nearly equal to the diameter of the lumen such that it fills the lumen but may be retracted through the lumen,
the elongated cylinder of introducer and cutting surface having a length longer than the cannula such that the cutting surface protrudes from the interior lumen of the cannula,
wherein the introducer further comprises a top portion,
the top portion being located on the proximal end of the cylinder,
the top portion having a diameter larger than the elongated cylinder of the introducer,
the top portion further having a diameter larger than the diameter of the cannula,
the top portion has a substantially flat surface oriented perpendicularly to the cylinder of the introducer;
and the bone preparation tool comprises:
an ergonomic handle assembly,
a flexible rod having a substantially cylindrical configuration with a curve complementary to the curved shaft of the cannula,
the flexible rod further having a diameter smaller than the diameter of the lumen;
the ergonomic handle assembly abutting the proximal end of the flexible rod; and
the flexible rod terminating distally in a bone preparation tip, wherein the bone preparing tip further comprises:
a flat bottom edge sharing a vertical axis with the rod before bending at a leading edge along a horizontal axis, the leading edge forming a wedge axis for a modified wedge,
the flat bottom edge forms the first substantially triangular shape of the wedge,
a first side wall and a second side wall form two substantially polygonal sides of the wedge and the third substantially polygonal side is shared with the rod,
the two side walls share a first edge with the flat bottom edge,
the two side walls share a second edge with the leading edge,
a third wall for the two side walls tapers from the rod,
dual cutting blades form a fourth edge of the side walls and are shaped substantially in the shape of a solid arch,
the dual surface cutting blades protrude from top edges of side polygonal faces of the wedge,
the arch of the cutting blades having a radius less than the radius of the lumen,
the rod having a radius less than the arch of the cutting blades,
the radius of the blades and the radius of the rod set at two distinct points relative to and off-set from one another in the horizontal axis.

6. A tool as described in claim 5 wherein the bone preparation tip affects bone positioned laterally from of the lumen shaft.

\* \* \* \* \*